:

US008246629B2

(12) United States Patent
Jonsson

(10) Patent No.: US 8,246,629 B2
(45) Date of Patent: Aug. 21, 2012

(54) FEEDING DEVICE FOR A MONOMER

(75) Inventor: Sören Jonsson, Linköping (SE)

(73) Assignee: Cemvac System AB (SE)

( * ) Notice: Subject to any disclaimer, the term of this patent is extended or adjusted under 35 U.S.C. 154(b) by 332 days.

(21) Appl. No.: 10/515,846

(22) PCT Filed: Mar. 31, 2003

(86) PCT No.: PCT/SE03/00515
§ 371 (c)(1),
(2), (4) Date: May 12, 2005

(87) PCT Pub. No.: WO03/101599
PCT Pub. Date: Dec. 11, 2003

(65) Prior Publication Data
US 2005/0228396 A1    Oct. 13, 2005

(30) Foreign Application Priority Data
Jun. 3, 2002 (SE) ........................ 0201673

(51) Int. Cl.
*A61B 17/58* (2006.01)
*A61B 17/60* (2006.01)
*A61F 2/00* (2006.01)
*A61M 5/00* (2006.01)
*B67D 1/00* (2006.01)

(52) U.S. Cl. .............................. 606/94; 604/187; 222/83

(58) Field of Classification Search ............. 606/92–95; 604/36–38, 82, 218, 187, 191, 227, 900, 604/54, 55, 71, 411; 222/134–137, 145.5, 222/83; 206/222
See application file for complete search history.

(56) References Cited

U.S. PATENT DOCUMENTS

| 346,096 A | * | 7/1886 | Horn .............................. 292/279 |
| 3,162,217 A | * | 12/1964 | Poli, Jr. et. al. ................. 141/27 |
| 3,557,784 A | * | 1/1971 | Shields ........................... 604/68 |
| 3,724,460 A | * | 4/1973 | Gomez et al. .................. 604/88 |
| 3,736,932 A | * | 6/1973 | Satchell ........................ 604/190 |
| 3,766,917 A | * | 10/1973 | Wimmer ........................ 604/88 |
| 3,767,085 A | * | 10/1973 | Cannon et al. .................. 222/82 |
| 3,828,980 A | * | 8/1974 | Creighton et al. ............ 222/137 |
| 4,040,420 A | * | 8/1977 | Speer ............................. 604/82 |
| 4,312,343 A | * | 1/1982 | LeVeen et al. ................ 604/211 |

(Continued)

FOREIGN PATENT DOCUMENTS
EP    1 016 452 A2    7/2000

*Primary Examiner* — Kevin T Truong
*Assistant Examiner* — David Bates

(57) ABSTRACT

A delivery device for a monomer may include an elongate container designed to enclose one or more ampoules containing the monomer. The elongate container may include: a connection at a first end of the elongate container for delivering the monomer to a mixing device, pre-filled with a polymer, for preparation of bone cement composition under vacuum; a cap at a second end of the elongate container; at least one air inlet aperture in a wall of the elongate container; and a manually actuatable element for opening the one or more ampoules. The manually actuatable element may include: a knob; a draw rod; and one or more spikes. The knob may be in threaded engagement with the draw rod. An end of the draw rod may extend past the one or more ampoules. Turning the knob may cause the one or more spikes to penetrate the one or more ampoules.

20 Claims, 1 Drawing Sheet

U.S. PATENT DOCUMENTS

| | | | | |
|---|---|---|---|---|
| 4,333,456 A * | 6/1982 | Webb | | 604/121 |
| 4,333,457 A * | 6/1982 | Margulies | | 604/121 |
| 4,461,325 A * | 7/1984 | Palau et al. | | 139/68 |
| 4,494,904 A * | 1/1985 | Hill et al. | | 414/491 |
| 4,631,055 A * | 12/1986 | Redl et al. | | 604/82 |
| 4,723,938 A * | 2/1988 | Goodin et al. | | 604/97.02 |
| 4,842,881 A * | 6/1989 | Kanemaru et al. | | 426/307 |
| 4,978,336 A * | 12/1990 | Capozzi et al. | | 604/82 |
| 5,161,301 A * | 11/1992 | Kilsdonk | | 29/739 |
| 5,161,715 A * | 11/1992 | Giannuzzi | | 222/82 |
| 5,273,190 A * | 12/1993 | Lund | | 222/83 |
| 5,290,259 A * | 3/1994 | Fischer | | 604/218 |
| 5,328,462 A * | 7/1994 | Fischer | | 604/82 |
| 5,378,233 A * | 1/1995 | Haber et al. | | 604/83 |
| 5,391,157 A * | 2/1995 | Harris et al. | | 604/208 |
| 5,458,448 A * | 10/1995 | Cheng | | 411/55 |
| 5,464,396 A * | 11/1995 | Barta et al. | | 604/191 |
| 5,478,323 A * | 12/1995 | Westwood et al. | | 604/191 |
| 5,582,596 A * | 12/1996 | Fukunaga et al. | | 604/191 |
| 5,808,511 A * | 9/1998 | Kobayashi | | 330/149 |
| 5,810,885 A * | 9/1998 | Zinger | | 606/213 |
| 5,827,262 A * | 10/1998 | Neftel et al. | | 604/414 |
| 5,866,122 A * | 2/1999 | Turecek et al. | | 424/94.64 |
| 6,065,645 A * | 5/2000 | Sawhney et al. | | 222/137 |
| 6,113,571 A * | 9/2000 | Zinger et al. | | 604/82 |
| 6,116,900 A * | 9/2000 | Ostler | | 433/89 |
| 6,165,201 A * | 12/2000 | Sawhney et al. | | 606/214 |
| 6,179,862 B1 * | 1/2001 | Sawhney | | 606/214 |
| 6,197,194 B1 * | 3/2001 | Whitmore | | 210/321.8 |
| 6,398,761 B1 * | 6/2002 | Bills et al. | | 604/191 |
| 6,471,670 B1 * | 10/2002 | Enrenfels et al. | | 604/88 |
| 6,508,791 B1 * | 1/2003 | Guerrero | | 604/183 |
| 6,571,992 B2 * | 6/2003 | Pierson et al. | | 222/390 |
| 6,840,921 B1 * | 1/2005 | Haider et al. | | 604/191 |
| 6,972,005 B2 * | 12/2005 | Boehm et al. | | 604/191 |
| 7,135,027 B2 * | 11/2006 | Delmotte | | 606/93 |
| 2002/0146662 A1 * | 10/2002 | Radl et al. | | 433/90 |
| 2003/0023202 A1 * | 1/2003 | Nielson | | 604/80 |
| 2003/0120217 A1 * | 6/2003 | Abergel | | 604/191 |
| 2003/0233067 A1 * | 12/2003 | McIntosh et al. | | 604/82 |

* cited by examiner

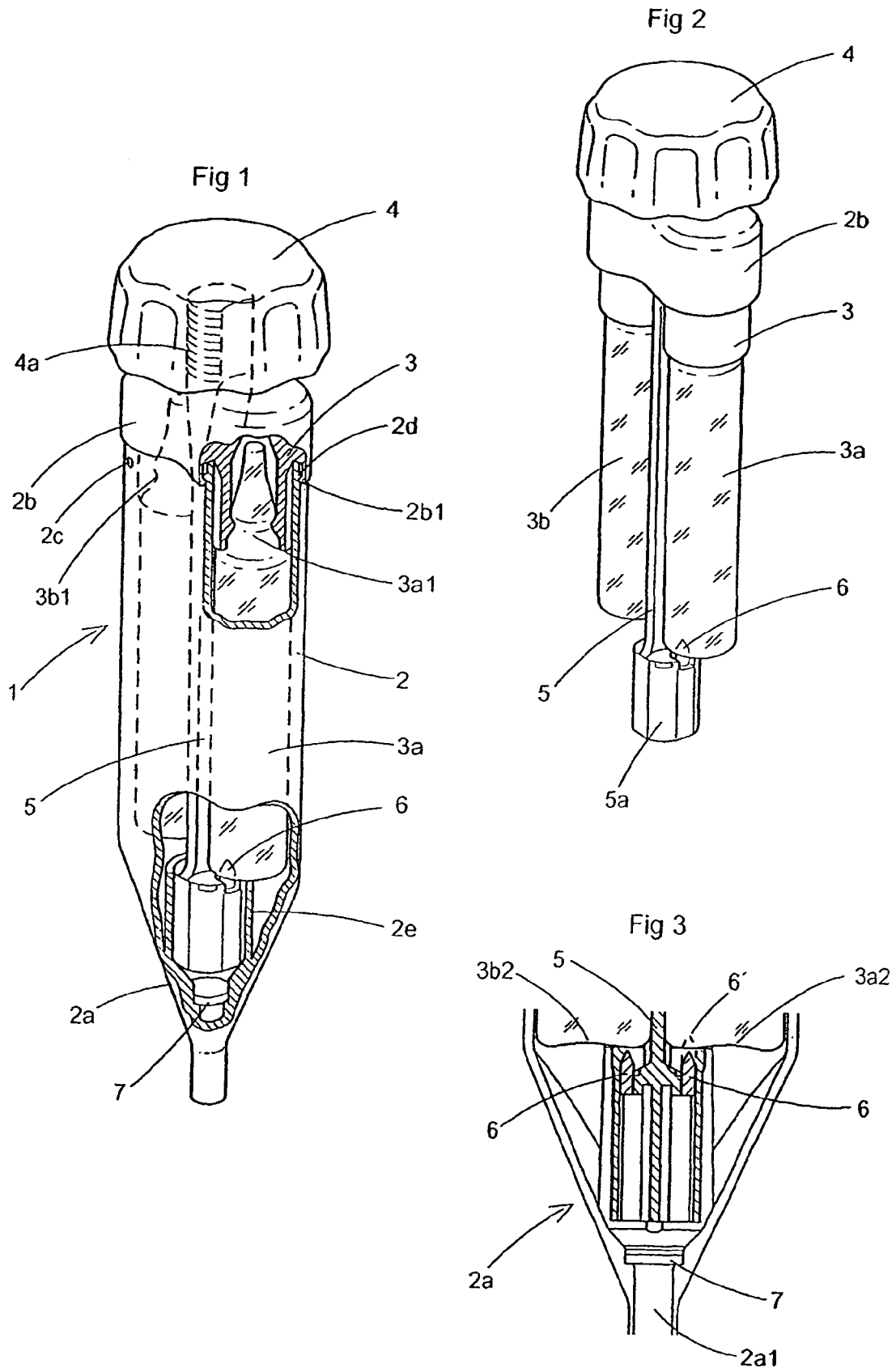

FEEDING DEVICE FOR A MONOMER

BACKGROUND

1. Field

The present invention relates to a device according to the pre-characterising clause of claim 1.

2. Description of Related Art

EP 1 016 452 A2 discloses a delivery device of the generic type. Although this device in itself functions quite satisfactorily, there is a desire to provide a delivery device for a monomer, which is easier to manufacture and handle than this known delivery device.

SUMMARY

The object of the present invention is to provide a delivery device that is improved in this respect and this is achieved by the features specified in the characterising part of claim 1.

The invention, which will be explained in more detail below with reference to the drawing attached, furthermore has one or more of the characteristics specified in the subordinate claims.

BRIEF DESCRIPTION OF THE DRAWINGS

In the drawing:

FIG. 1 shows an embodiment of a delivery device according to the invention, partially in section, FIG. 2 shows a detailed view of the holder and penetration element according to FIG. 1, and FIG. 3 shows a detailed view of the said penetration element.

DETAILED DESCRIPTION OF EXAMPLE EMBODIMENTS

In the drawing, 1 generally denotes a delivery device for a monomer comprising an elongate container 2, which at one end is provided with a funnel-shaped connection 2a to a mixing device, not shown in the drawing, and which at its other end has a removable cap 2b, which preferably has snap elements 2b1 interacting with corresponding snap elements 2d on the container. The mixing device is of a type, for example, which is described in more detail in EP 1 016 452 A2, in which a polymer, with which the mixing container has been pre-filled, is mixed under a vacuum with a monomer for the preparation of bone cement.

The container 2, which in the embodiment shown in the drawing has an air inlet aperture 2c adjacent to the cap 2b, is designed to enclose at least one and up to three ampoules. The embodiment shown in the drawing the container encloses two ampoules 3a, 3b.

Operatively connected to the removable cap 2b is a holder 3, designed to hold the ampoules 3a, 3b in a predefined position in the container 2 by means of a positively interlocking engagement around the necks 3a1, 3b1 of the ampoules 3a, 3b.

Also operatively connected to the openable cap 2b are manually actuatable elements for opening the ampoules 3a, 3b. The said elements comprise a knob 4, which is in threaded engagement 4a with a rod 5 carried through cap 2b. At its remote end, the rod 5 has a holder 5a for metal spikes 6 pointing towards the base 3a2, 3b2 of each ampoule. For the holder 5a there is a guide 2e of a complementary shape to that of the holder 5a.

The distance of the metal spikes 6 from the base 3a2, 3b2 of each ampoule is adjustable. It will be appreciated that manually turning the knob 4 reduces the distance between the spikes 6 and the base 3a2, 3b2 of each ampoule until the spikes 6 ultimately penetrate the bases of the ampoules. An identical distance between the spikes and the base 3a2, 3b2 of each ampoule naturally produces simultaneous penetration, but by selecting a different distance between the spikes 6 and the base 3a2, 3b2 of each respective ampoule the ampoule bases will be audibly penetrated at different times in succession. FIG. 3 illustrates with a dashed line a spike 6' which, for example, has been assigned a shorter distance from the base of the ampoule than the other spike 6.

Also worth noting from FIGS. 1 and 3 is a filter 7, designed to prevent glass splinters from the ampoules 3a, 3b reaching the delivery duct 2a1 of the connection 2a.

As will be apparent from the description above, the device according to the invention is made up of few parts and has a particularly simple and reliable method of handling. When it is to be used, the requisite number of ampoules 3a, 3b for the desired quantity of bone cement are inserted into the holder 3, which holds them fast at the necks 3a1, 3b1, there being a distance between the spikes 6 and the base 3a2, 3b2 of each ampoule large enough to prevent accidental penetration. The ampoules 3a, 3b thus fixed to the cap 2b are inserted into the container 2 far enough for the user to distinctly hear the cap 2b snap tight to the container 2.

The delivery device 1 is then connected by its connection 2a to the mixing vessel where, under the vacuum there prevailing, air can flow through the container 2 via the air inlet aperture 2c.

Turning the knob 4 causes the ampoules to be successively penetrated, preferably audibly, and the monomer contained in the ampoules is carried down into the mixing vessel by the air flowing through the container 2.

The further process of preparing bone cement is well-known and will therefore not be further explained here.

The invention claimed is:

1. A delivery device for a monomer, comprising:
   a container having a delivery duct at a distal end and an opening at a proximal end;
   at least one ampoule containing the monomer disposed within the container, the at least one ampoule having a proximal end and a distal end;
   a rod having a proximal end that extends through the opening in the container and a distal end disposed within the container, wherein the rod is not rotatable relative to the at least one ampoule;
   at least one spike connected to the distal end of the rod, the at least one spike disposed between the delivery duct and the distal end of the at least one ampoule; and
   a knob threadably engaged with the proximal end of the rod, the knob being rotatable relative to the rod from a first position, whereat the piercing end of the at least one spike is spaced apart from the at least one ampoule, to a second position, whereat the piercing end of the at least one spike penetrates the at least one ampoule.

2. The delivery device of claim 1, wherein the container comprises a distal portion and a cap, the cap having the opening at the proximal end.

3. The delivery device of claim 2, comprising a holder configured to engage the cap and to retain the proximal end of the at least one ampoule.

4. The delivery device of claim 2, wherein the cap and distal portion are snap-fit together.

5. The delivery device of claim 1, wherein the at least one spike penetrates the distal end of the at least one ampoule when the actuator is at the second position.

6. The delivery device of claim 1, wherein the container has at least one air inlet aperture in a wall of the container.

7. The delivery device of claim 1, wherein the container is elongate and has a funnel-shaped distal end.

8. The delivery device of claim 1, comprising a filter disposed between the at least one ampoule and the delivery duct.

9. The delivery device of claim 1, comprising a first ampoule and a second ampoule disposed within the container, the first ampoule and second ampoule being spaced apart within the container; a first spike disposed between the delivery duct and the distal end of the first ampoule; and a second spike disposed between the delivery duct and the distal end of the second ampoule.

10. The delivery device of claim 9, wherein the first spike, second spike and rod are configured such that the distance between the distal end of the first spike and the proximal end of the rod is less than the distance between the distal end of the second spike and the proximal end of the rod.

11. The delivery device of claim 9, wherein the first spike is longer than the second spike.

12. The delivery device of claim 9, wherein at least a portion of the rod is disposed between the first ampoule and the second ampoule.

13. The delivery device of claim 1, wherein the container has a longitudinal axis, and the rod is substantially aligned with the longitudinal axis.

14. The delivery device of claim 13, wherein the rod has a first portion at the proximal end of the rod having a first diameter threadably engaged with the knob, and a second portion, intermediate the first portion and the distal end of the rod, having a second diameter.

15. The delivery device of claim 9, wherein the rod has a first portion at the proximal end of the rod having a first diameter threadably engaged to the knob, and a second portion, intermediate the first portion and the distal end of the rod, having a second diameter, the second diameter being less than the first diameter.

16. A delivery device for a monomer, comprising:
a container having a delivery duct at a distal end and an opening at a proximal end;
at least one ampoule containing the monomer disposed within the container, the at least one ampoule having a proximal end and a distal end;
a rod having a proximal end that extends through the opening in the container and a distal end disposed within the container, wherein the rod is not rotatable relative to the at least one ampoule;
at least one spike connected to the distal end of the rod, the at least one spike disposed between the delivery duct and the distal end of the at least one ampoule, the at least one spike having a piercing end; and
an actuator rotatable attached to the proximal end of the rod, the actuator being rotatable from a first position, whereat the piercing end of the at least one spike is spaced apart from the at least one ampoule, to a second position, whereat the piercing end of the at least one spike penetrates the at least one ampoule.

17. The delivery device of claim 16, wherein the at least one spike penetrates the distal end of the at least one ampoule when the actuator is at the second position.

18. The delivery device of claim 16, wherein the actuator is a knob threadably connected to the proximal end of the rod.

19. The delivery device of claim 16, comprising a first ampoule and a second ampoule disposed within the container, the first ampoule and second ampoule being spaced apart within the container; a first spike disposed between the delivery duct and the distal end of the first ampoule; and a second spike disposed between the delivery duct and the distal end of the second ampoule.

20. The delivery device of claim 19, wherein at least a portion of the rod is disposed between the first ampoule and the second ampoule.

\* \* \* \* \*